(12) United States Patent
Yamaguchi

(10) Patent No.: US 6,473,177 B2
(45) Date of Patent: Oct. 29, 2002

(54) PARTICLE-SIZE DISTRIBUTION MEASURING APPARATUS

(75) Inventor: Tetsuji Yamaguchi, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/876,505

(22) Filed: Jun. 6, 2001

(65) Prior Publication Data

US 2002/0003624 A1 Jan. 10, 2002

(30) Foreign Application Priority Data

Jul. 7, 2000 (JP) ........................... 2000-207358

(51) Int. Cl.[7] ............................................... G01N 15/02
(52) U.S. Cl. ......................................... 356/336; 356/335
(58) Field of Search ........................... 356/335, 336, 356/338, 340, 341

(56) References Cited

U.S. PATENT DOCUMENTS

| | | | | |
|---|---|---|---|---|
| 5,015,094 A | * | 5/1991 | Oka et al. ................. | 356/335 |
| 6,211,956 B1 | * | 4/2001 | Nicoli ....................... | 356/337 |
| 6,275,290 B1 | * | 8/2001 | Cerni et al. ................ | 356/335 |
| 6,354,913 B1 | * | 3/2002 | Miyashita et al. .......... | 451/41 |

FOREIGN PATENT DOCUMENTS

| | | |
|---|---|---|
| JP | 61-178643 | 8/1986 |
| JP | 05-113396 | 5/1993 |

\* cited by examiner

*Primary Examiner*—Georgia Epps
*Assistant Examiner*—Saeed H Seyrafi
(74) *Attorney, Agent, or Firm*—Oppenheimer, Wolff & Donnelly LLP

(57) ABSTRACT

The present invention presents a particle-size distribution measuring apparatus which allows measuring simultaneously the dispersion state of particles in suspension medium and the particle-size distribution of the particles. The present invention is a particle-size distribution measuring apparatus which measures the particle-size distribution of particles included in a sample. The particle-size distribution measuring apparatus comprises a pH meter for measuring the pH value of the sample and an information processing portion which determines the relation between the pH value and the particle-size distribution on the basis that the pH value measured by the pH meter and the measured particle-size distribution are in the same state.

12 Claims, 2 Drawing Sheets

PARTICLE-SIZE DISTRIBUTION MEASURING APPARATUS

FIELD OF THE INVENTION

The present invention relates to a particle-size distribution measuring apparatus, and particularly to an apparatus in which the pH value is measured and the state of the particle dispersion can be monitored from the pH value and which allows calculating an ideal pH value for obtaining an ideal particle-size distribution state therefrom.

DESCRIPTION OF THE PRIOR ART

In the prior art for managing the product quality in each of the production steps in a factory, a batch test using a particle-size measuring apparatus is conventionally employed. In such a batch test, a particle-size measuring apparatus extracts a batch sample (i.e. specimen to be measured) and measures the particle-size distribution thereof. Namely an operator in the factory extracts some quantity of a sample to be measured (hereinafter referred to as "sample") by particle-size distribution measuring apparatus from the piping in the factory. Then, he or she introduces the sample into the particle-size distribution measuring apparatus and executes the measurement. Corresponding to the result of the measurement, it is decided whether a correct and proper working material is supplied to each of the production steps in the factory.

For example, there is a case in which an abrasive material for grinding wafers is supplied as a working material through piping in a factory. If this abrasive material aggregates, the aggregated abrasive material may create flaws on the surface of wafers. Thus, it is conventional to measure the particle-size distribution of the abrasive material to avoid such unfavorable incidents which may occur during such a fabrication process.

When particles are in a dispersion state, the surrounding medium and ionicity have a greater effect on smaller particles, which leads to an aggregation of the particles. Thus, also in the prior art, the pH value of the extracted sample is measured in order to estimate the influence of charges and ionicity. Also, the degree of the dispersion is estimated according to the measured particle-size distribution in the same state.

However, the aforementioned measurements of the pH value and the particle-size distribution are carried out using separate apparatuses, and the data of those measurements are outputted separately. Thus, it is difficult to find the correlation between the pH value and the particle-size distribution. Another problem is that the particle-size distribution and the degree of dispersion of the corresponding sample can not be measured simultaneously.

The present invention takes into consideration the aforementioned problems in the prior art. An object of the present invention is to propose a particle-size distribution measuring apparatus which allows measuring simultaneously the dispersion state of particles in the suspension medium and the particle-size distribution.

SUMMARY OF THE INVENTION

In order to resolve the aforementioned problems, the particle-size distribution measuring apparatus according to the present invention measures particle-size distribution of particles included in a sample, and further comprises a pH meter for measuring the pH value of the sample and an information processing portion. The information processing portion determines the relation between the pH value and the particle-size distribution on the basis that the pH value measured by the pH meter and the measured particle-size distribution are in the same state.

The information processing portion determines the relation between the dispersion state of the sample and the particle-size distribution based on the measured value of the pH meter and the measured particle-size distribution. Therefore, the properties of the sample can be more accurately determined. As a result, it is possible to calculate a pH value which permits maintaining a state having a desired particle-size distribution.

It is possible to change the dispersion state of a sample by monitoring and adjusting the pH value of a sample which is introduced into the particle-size distribution measuring apparatus. Or, inversely, it becomes possible to obtain a desired dispersion state and a particle-size distribution of the particles by monitoring the particle-size distribution and by changing the pH value.

In both cases, the change of the pH value and the particle-size distribution can be simultaneously and properly measured in a same state. Therefore, the reliability of the measured value can be improved.

In a case that the particle-size distribution measuring apparatus further comprises a preparation portion for previously adjusting the pH value of the sample by adjusting the pH value of a sample by the preparation portion in a sequential manner, from the change of the particle-size distribution corresponding to each of the pH values, the relation between them is automatically obtained in a sequential manner.

In a case that the information processing portion is connected with a host information processing system in the factory so that they can communicate mutually, and by which the information processing portion outputs the result of the measurement of the particle-size distribution to the host information processing system, the system can manage the fabrication processes in the factory. The host information processing system can manage each fabrication process more accurately, using the relation between the dispersion state and the particle-size distribution of the sample measured by the particle-size distribution measuring apparatus. For example, when particles dispersed in a dispersion medium as working material is supplied via piping in a factory, an ideal pH value for making an ideal particle-size distribution of the particles is obtained. The pH value can be adjusted according to the ideal pH value. Therefore, a high preciseness working can be assured, correspondingly.

DETAILED DESCRIPTION OF THE PREFERRED EMBODIMENT

Figure 1:
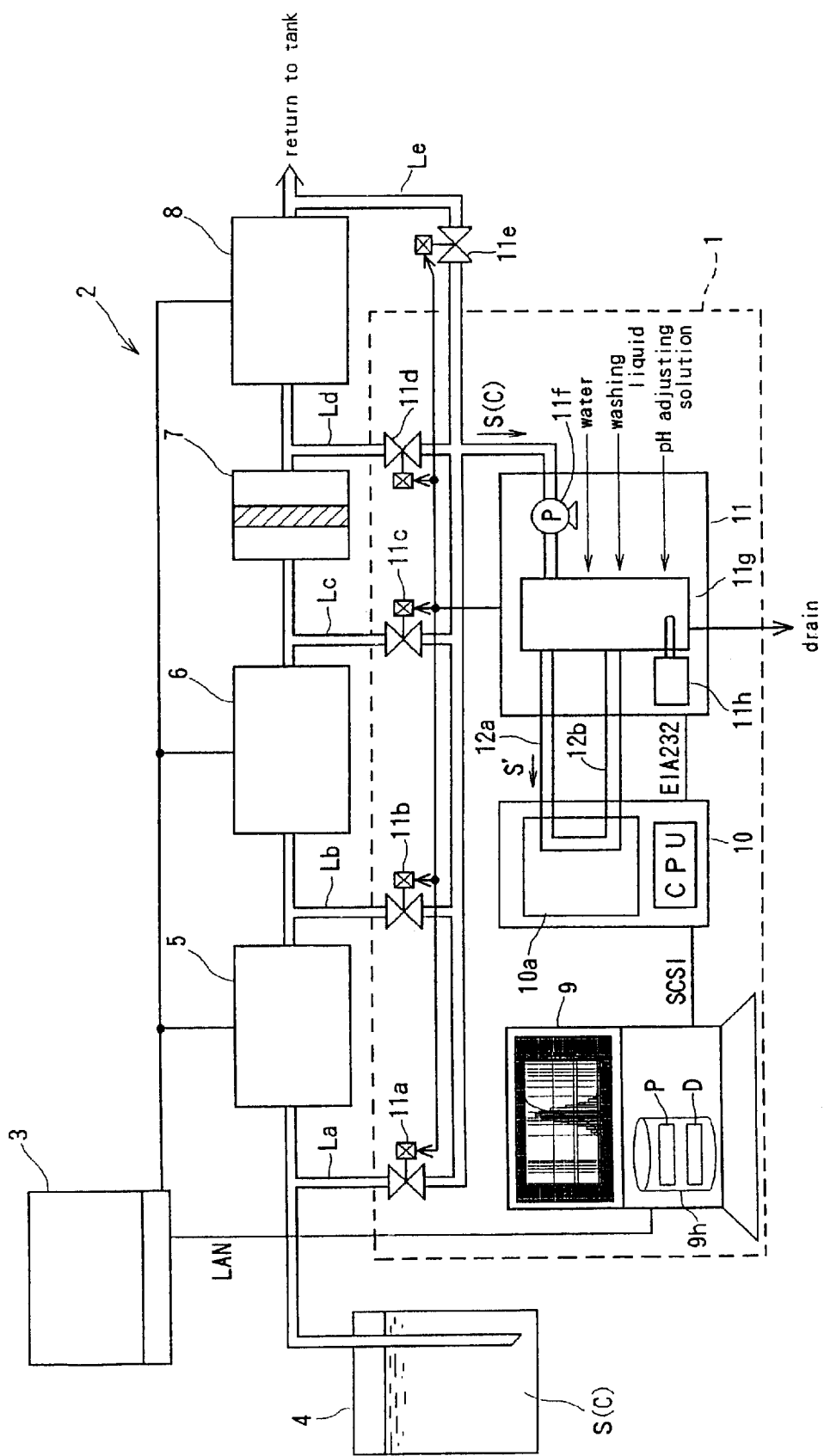
FIG. 1 is an example of a particle-size distribution measuring apparatus according to the present invention.

Referring to FIG. 1, an embodiment of the particle-size distribution measuring apparatus according to the present invention is described below. In FIG. 1, reference numeral 2 denotes a factory in which the production processes are managed using a particle-size distribution measuring apparatus 1 according to the present invention. The example shows a process in which semiconductor wafers are polished using an abrasive material C. Reference numeral 3 denotes a host information processing system (hereinafter referred to as host PC 3) which controls the processes in the factory 2. Reference numeral 4 denotes a tank for storing the abrasive material C, and reference numeral 5 denotes a dispersing portion for stirring the abrasive material C supplied from the tank 4 using ultrasonic sound. Reference numeral 6 denotes a pH adjusting portion for adjusting the pH value of the stirred abrasive material C, reference numeral 7 denotes a filter for separating the scraping or solid chips from the abrasive material, and reference numeral 8 denotes a polishing portion for polishing the wafers using the abrasive material C.

Reference numeral 9 denotes an information processing portion for controlling the particle-size distribution measuring apparatus 1. Reference numeral 10 denotes a portion for measuring the particle-size distribution which is, for example, a dynamical light scattering type referred hereinafter to simply as a particle-size distribution measuring portion. Reference numeral 11 denotes a preparation portion which changes the sample S to a sample S' suitable for measuring the particle-size distribution. The sample S' will be measured by the particle-size distribution measuring portion 10.

The particle-size distribution measuring portion 10 and the preparation portion 11 are connected mutually through piping 12a and 12b for flowing the sample solution S' to be measured. The information processing portion 9 and the particle-size distribution measuring portion 10 as well as particle-size distribution measuring portion 10 and the preparation portion 11 are connected mutually through communication lines SCSI and EIA232. The communication lines are referenced to the Regulations of SCSI and EIA232, respectively.

In this example, the particle-size distribution measuring apparatus 1 comprises: the information processing portion 9, the particle-size distribution measuring portion 10, and the preparation portion 11. Control signals from the information processing portion 9 are transmitted to the particle-size distribution measuring portion 10 and preparation portion 11 through the communication lines SCSI and EIA232.

It is noted that communication between the information processing portion 9, particle-size distribution measuring portion 10 and the preparation portion 11 is not limited to the Regulations of SCSI and EIA232, but arbitrary communication can be employed in place of them. It is also obvious that the particle-size distribution measuring apparatus can be modified and realized in a variety of arrangements in the scope of the present invention. For example, the information processing portion 9 can be directly connected to the preparation portion 11 and/or a pH meter 11h which will be described hereinafter.

The information processing portion 9 is connected to the host PC 3 through a LAN (Local Area Network) system, for example. The values measured by the particle-size distribution measuring apparatus 1 are outputted to the host PC 3 and are used as information for controlling the fabrication processes.

The host PC 3 controls the dispersing portion 5, pH adjusting portion 6 and the polishing portion 8 so that the process flow in each of them can be regulated. The host PC 3 monitors fabrication process control information sent from the information processing portion 9, and the host PC 3 determines whether appropriate working material (i.e., abrasive material C) necessary for each of the processes is supplied or not. When the state of the abrasive material C is bad, the host PC 3 stops the corresponding process.

The information processing portion 9 comprises conventional components, for example, CPU and memory. The information processing portion 9 further comprises a sequence executing program P for executing a measuring sequence which controls the particle-size distribution apparatus 1, and further comprises a memory medium 9h for storing measuring sequence data D. The measuring sequence data D is read out and executed by the sequence executing program P. The memory medium 9h belongs to a type which can be read out by a computer.

The memory medium 9h in this embodiment is a hard disc, for example. In order to operate the information processing portion 9, the executing program P stored in the hard disc is copied onto a memory (not shown) and is executed. The present invention does not restrict the detailed constitution of the information processing portion 9. Therefore, the description and the illustration of the inner structure of the information processing portion are omitted, but it is obvious that it contains a memory, CPU and interfaces, etc.

Branching piping La thru Le are disposed at a respectively appropriate position in the processing piping of abrasive material C. Solenoid valves 11a thru 11e are disposed in the branching piping La thru Le. A pump 11f for sucking sample is disposed downstream of the solenoid valves 11a thru 11e.

The solenoid valves 11a thru 11e are controlled by the output signals from the preparation portion 11. When the pump 11f is activated under a condition in which at least one of the solenoid valves 11a thru 11e is open, a predetermined quantity of sample S to be measured (i.e., abrasive material C in this embodiment) is sucked into the preparation portion 11.

Namely, the solenoid valves 11a thru 11e and the sample sucking pump 11f constitute a sampling portion for taking in the sample S to be measured, and the information processing portion 9 communicates and controls the sampling portion 11a thru 11f. Each branching piping La thru Le is located such that a sample S is sampled from the piping in the factory. Because the sampling portion contains a pump 11f, the sample S can be sucked out. As a result, a sample S to be measured can be sampled from the tank 4 where abrasive material C is stored.

Reference numeral 11g denotes an adjusting container in which the sample S taken in by the sampling portion 11a thru 11f is mixed with water (i.e. solvent) so that the concentration is adjusted and/or pH value is adjusted using pH adjusting solution (acid or basic solution for pH adjustment). Reference numeral 11h denotes a pH meter which measures the pH value of the sample S' in the adjusting container 11g. Namely, the sample S taken into the preparation portion 11 is adjusted by the pH adjusting solution and/or solvent in the adjusting container 11g. Further treatments, for example, are carried out in the adjusting container 11g by an ultrasonic dispersion treatment and circulation dispersion, etc. As a result of the preparation which are necessary for the particle-size distribution measurement, the sample S becomes a sample S' to be measured.

The sample S' adjusted in the adjusting container 11g is sent to a flow-cell 10a in the particle-size distribution measuring portion 10 via piping for sample 12a. After the measurement, the effluent of the sample S' is returned to the adjusting container 11g via piping for sample 12b. Namely, in this embodiment, the sample S' circulates between the particle-size distribution measuring portion 10 and the preparation portion 11.

The value measured by the pH meter 11h is transferred to the information processing portion 9 through the communication lines EIA232 and SCSI, etc. The information processing potion 9 controls the sequence of the preparation in the preparation portion 11 through the communication lines EIA232 and SCSI. Because the preparation in the preparation portion 11 is executed by a sequence control, which is predetermined by the measurement sequence data D, the repeatablity of the measurement of the particle-size distribution is assured.

When the preparation by the preparation portion 11 is completed, the pH meter 11h measures the pH value. The system determines whether the measurement of the particle-size distribution shall be started from the obtained pH value. If the pH value obtained by the pH meter 11h is out of range, the pH value is adjusted using pH adjusting solution under the control of the information treatment portion 9 to achieve an ideal particle-size distribution. It is possible, simultaneously, to adjust the sequence control for the preparation by varying the measurement sequence data D.

Figure 2:
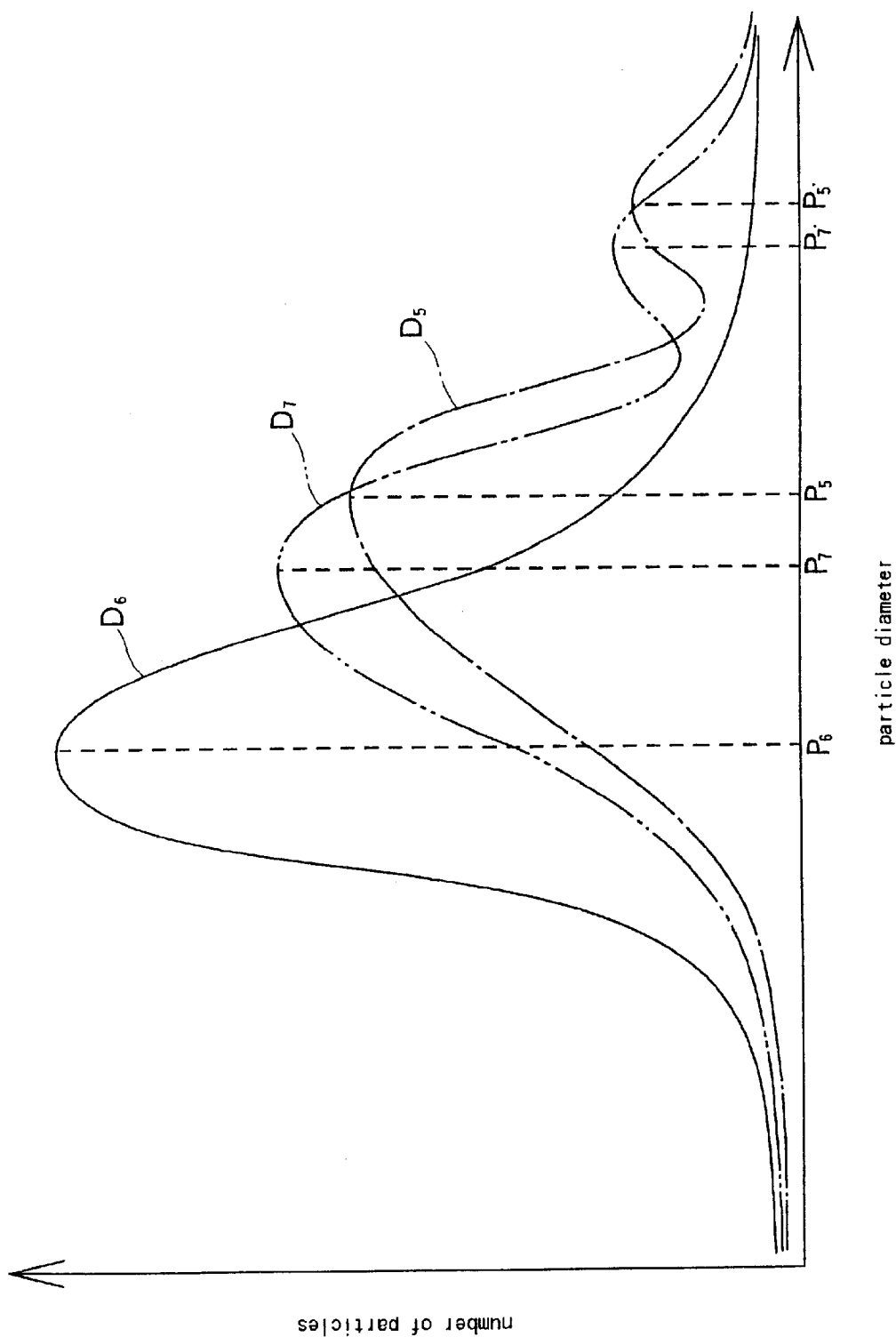
FIG. 2 is a graph illustrating an example of the correlation relation between the pH value and the particle-size distribution, which are measured using the particle-size distribution measuring apparatus of FIG. 1.

FIG. 2 is a graph illustrating examples of the correlation relation between the pH value and the particle-size distribution of the solution S'. The abscissa of the graph is the particle diameter and the ordinate is the number of particles. The solid line curve $D_6$ shows a particle-size distribution of solution S' when the pH value is 6. The one-point dotted line curve $D_5$ shows a particle-size distribution of the solution S' when the pH value is 5. And the two-point dotted line $D_7$ shows a particle-size distribution S' when the pH value is 7.

FIG. 2 illustrates sample S' having the best dispersion when its pH value is 6. When the pH value shifts from the value of 6, dispersion deteriorates and aggregation begins. The peak of the particle-size distribution shifts to the peaks $P_5$ or $P_7$, which are found at a larger particle-size range compared to the peak at the pH value of 6. And each of the particle-size distributions $D_5$, $D_7$ has a sub-peak $P_5'$ and $P_7'$ which have a larger particle-size range.

For the particles shown in this example, the dispersion is optimal at the pH value of 6. Thus, the information processing portion 9 controls the mixing of the pH adjusting solution so that the sample S' having a pH value of 6 is generated by the preparation in the preparation portion 11. In this way, a sample S' in a dispersion state without aggregation can be generated.

It is noted that the pH meter 11h is disposed in the adjusting container 11g for the precedent example. The scope of the present invention is not limited to arrangement of the pH meter described above. The pH meter 11h can be disposed at an arbitrary position in the flow path of the sample S', for example, in the sample piping 12a, 12b, or in the flow cell 10a.

In the precedent description, sample S', which becomes a dispersion state without aggregation when the pH value is 6, is described as an example. However, when the correlation between the particle-size distribution and the pH value is not known, the correlation can be obtained using the particle-size distribution apparatus 1.

For example, the sequence control according to the measurement sequence data D may change stepwise the set value of the pH value in the preparation portion 11 and control the system so as to measure the corresponding particle-size distribution. In such a case, according to a series of sequence controls, it is possible to obtain the correlation between the particle-size distribution and the pH value which is not known for the relevant sample particles. Thus, it is possible to determine the optimal value of the pH value for obtaining a desirable dispersion state of the sample S'.

Further, the information processing portion 9 in the example described above is connected with the host PC 3 at the factory so that the result of the particle-size distribution measurement is transferred to the host PC 3. The information processing portion 9 measures the correlation between the particle-size distribution and the pH value for each of the samples S and transfers the result to the host PC 3. The host PC 3 can execute some determination in connection with the preparation of working material in the factory process based on the correlation between the particle-size distribution and the pH value. However, the scope of the present invention is not limited to such an embodiment.

After the particle-size distribution measuring portion 10 measures the correlation between the particle-size distribution and the pH value, the adjusting container 11g has a function to drain the effluent of the measured sample S' under the control of the information processing portion 9. Washing liquid, for example, treatment solution, etc is supplied to the adjusting container 11g so that the adjusting container 11g and the particle-size distribution portion 10 are washed after the measurement.

In the precedent example, only the change of the pH value and corresponding particle-size distribution of the sample S' are measured. However, it is possible to measure the particle-size distribution of the sample S' as a function of time, wherein a time dependent particle-size distribution can be measured. It is also possible to measure the temperature dependency of the particle-size distribution. As a result, it is possible to determine the influence of the simultaneous change of the temperature and pH value to the particle-size distribution.

A display program may be stored in the memory 9h of the information processing portion 9 in order to display the state of the sample S' under the reaction when the pH value and/or temperature of the sample S are changed. Such state may be displayed in the display of the information processing portion 9. In such a case, users can easily determine which treatment is being carried out by the particle-size distribution measuring apparatus because the information about the state of the solution S' is displayed in the display.

In the aforementioned example, the sampling portion for taking in the sample S uses the solenoid valves 11a thru 11e and sucking pump 11f. However, the scope of the present invention is not limited to this example. For example, the sampling portion for taking in the sample S can comprise an auto-sampler which comprises a plurality of bottles for sampling the sample S and storing it therein, and one of the bottles is automatically selected and sent to the preparation portion 11.

In the aforementioned example, the units constituting the particle-size distribution measuring apparatus 1, namely the particle-size distribution measuring portion 10 and the preparation portion 11, are described as independent units. However, of course, they can be formed as an integrated apparatus in which the units are integrated. In the same way, it is not necessary to form the information processing portion 9 independently using a general use computer. The portion can be formed using an incorporation type microcomputer.

In the aforementioned example, the particle-size distribution measuring portion 10 measures the particle-size distribution using dynamic light scattering. However, the scope of the present invention is not limited to this example. For example, the particle-size distribution measuring portion can measure particle-size distribution using laser light diffraction/scattering.

By using the particle-size distribution apparatus according to the present invention, the relation between the dispersion state and the particle-size distribution can be obtained based on the measured pH value and the measured particle-size distribution. Thus, the properties of the sample can be more exactly known, correspondingly. Furthermore, it becomes possible to calculate the pH value which allows maintaining the desired state of the particle-size distribution. Still further, a change in the pH value and particle-size distribution can be measured in an exactly simultaneous state; thus, the reliability of the measurement can be improved, correspondingly.

What is claimed is:

1. A particle-size distribution measuring apparatus to measure particle-size distribution of particles in a sample, comprising:

a pH meter measuring the pH value of the sample; and an information processing portion coupled to the pH meter, the information processing portion determining the relation between the pH value and the particle-size distribution;

wherein the relation is based on the pH value measured by the pH meter being in the same state as the measured particle-size distribution.

2. The particle-size distribution measuring apparatus of claim 1, further comprising a preparation portion to previously adjust the pH value of the sample.

3. The particle-size distribution measuring apparatus of claim 2, further comprising:

a host information processing system coupled to the information processing portion at the factory to allow mutual communication;

wherein the information processing portion outputs the result of the measurement of the particle-size distribution to the host information processing system such that the host information processing system manages the fabrication processes at the factory.

4. The particle-size distribution measuring apparatus of claim 3, wherein the preparation portion sequentially adjusts the pH value of the sample.

5. The particle-size distribution apparatus of claim 4, wherein the host information processing system determines an ideal pH value to optimize the particle-size distribution of the sample, and wherein the information processing system adjusts the sample to the ideal pH value.

6. The particle-size distribution measuring apparatus of claim 1, further comprising:

a host information processing system coupled to the information processing portion at the factory to allow mutual communication;

wherein the information processing portion outputs the result of the measurement of the particle-size distribution to the host information processing system such that the host information processing system manages the fabrication processes at the factory.

7. The particle-size distribution measuring apparatus of claim 6, wherein the preparation portion sequentially adjusts the pH value of the sample.

8. The particle-size distribution apparatus of claim 7, wherein the host information processing system determines an ideal pH value to optimize the particle-size distribution of the sample, and wherein the information processing system adjusts the sample to the ideal pH value.

9. A method for controlling the dispersion state of a sample having particles, comprising:

simultaneously monitoring the pH value and particle-size distribution of the sample;

determining the relation between the pH value and the particle-size distribution on the basis that the measured pH value and measured particle-size distribution are in a same state;

determining the optimal pH value to maintain the particle-size distribution at a desired particle-size distribution.

10. The method of claim 9, further comprising:

maintaining the sample at the optimal pH value.

11. The method of claim 10, further comprising:

adjusting the pH value in a sequential manner.

12. The method of claim 11, further comprising:

coupling an information processing portion with a host information processing system at a factory;

wherein the host information processing system manages the fabrication processes of the factory.

* * * * *